(12) United States Patent
Nazarian et al.

(10) Patent No.: US 8,858,454 B2
(45) Date of Patent: Oct. 14, 2014

(54) MOTION CANCELLATION OF OPTICAL INPUT SIGNALS FOR PHYSIOLOGICAL PULSE MEASUREMENT

(75) Inventors: Richard A. Nazarian, Excelsior, MN (US); Lori E. Lucke, Eagan, MN (US); Susan S. Alfini, Champlin, MN (US); Mark J. Bina, Shoreview, MN (US); Don W. E. Evans, St. Paul, MN (US); Paul Harris, Delta (CA); Michael W. Geatz, Maple Grove, MN (US)

(73) Assignee: Basis Science, Inc., San Francisco, CA (US)

( * ) Notice: Subject to any disclaimer, the term of this patent is extended or adjusted under 35 U.S.C. 154(b) by 428 days.

(21) Appl. No.: 13/182,352

(22) Filed: Jul. 13, 2011

(65) Prior Publication Data

US 2012/0004519 A1 Jan. 5, 2012

Related U.S. Application Data

(63) Continuation of application No. 11/250,011, filed on Oct. 13, 2005, now Pat. No. 7,993,276.

(60) Provisional application No. 60/696,858, filed on Jul. 6, 2005, provisional application No. 60/681,397, filed on May 16, 2005, provisional application No. 60/619,253, filed on Oct. 15, 2004.

(51) Int. Cl.
*A61B 5/02* (2006.01)
*A61B 5/024* (2006.01)
*A61B 5/00* (2006.01)

(52) U.S. Cl.
CPC ............. *A61B 5/721* (2013.01); *A61B 5/02438* (2013.01); *A61B 5/7239* (2013.01)
USPC ............................ 600/500; 600/309; 600/310

(58) Field of Classification Search
USPC .......... 600/301, 323, 310, 393, 493, 500–504
See application file for complete search history.

(56) References Cited

U.S. PATENT DOCUMENTS

| | | | | |
|---|---|---|---|---|
| 4,281,645 A | * | 8/1981 | Jobsis | 600/324 |
| 4,338,950 A | | 7/1982 | Barlow, Jr. et al. | |
| 4,800,495 A | * | 1/1989 | Smith | 600/322 |
| 5,246,002 A | * | 9/1993 | Prosser | 600/336 |
| 5,431,170 A | | 7/1995 | Mathews | |
| 5,632,272 A | * | 5/1997 | Diab et al. | 600/323 |
| 5,634,080 A | * | 5/1997 | Kikinis et al. | 710/73 |
| 5,697,374 A | | 12/1997 | Odagiri et al. | |
| 5,776,070 A | | 7/1998 | Kitazawa et al. | |

(Continued)

OTHER PUBLICATIONS

Patent Abstracts of Japan, & JP 2004 283228 A (Seiko Epson Corp.), Dec. 5, 2003, vol. 2003, No. 12. (A11 is US counterpart claiming priority to JP 2004 283228 A).

(Continued)

*Primary Examiner* — Michael D'Angelo
(74) *Attorney, Agent, or Firm* — Fenwick & West LLP

(57) ABSTRACT

A pulse rate sensor that includes an accelerometer for measuring periodic motion and a piezo sensor for detecting erratic motion is capable of more accurately determining pulse rate by accounting for these types of motion. The pulse rate sensor in accordance with the present invention diminishes pulse rate signal degradation due to erratic motion through a combination of algorithms that control signal boosting, waveform refinement and signal noise suppression.

8 Claims, 6 Drawing Sheets

(56) References Cited

U.S. PATENT DOCUMENTS

| | | | |
|---|---|---|---|
| 5,807,267 A | 9/1998 | Bryars et al. | |
| 6,023,662 A | 2/2000 | Hayakawa et al. | |
| 6,099,478 A | 8/2000 | Aoshima et al. | |
| 6,129,676 A | 10/2000 | Odagiri et al. | |
| 6,361,501 B1 | 3/2002 | Amano et al. | |
| 6,721,584 B2 * | 4/2004 | Baker et al. | 600/323 |
| 7,018,338 B2 * | 3/2006 | Vetter et al. | 600/503 |
| 2002/0165462 A1 * | 11/2002 | Westbrook et al. | 600/529 |
| 2004/0034293 A1 | 2/2004 | Kimball | |
| 2004/0059236 A1 * | 3/2004 | Margulies et al. | 600/500 |
| 2004/0116969 A1 * | 6/2004 | Owen et al. | 607/6 |
| 2004/0236233 A1 * | 11/2004 | Kosuda et al. | 600/485 |
| 2005/0116820 A1 | 6/2005 | Goldreich | |
| 2006/0122521 A1 * | 6/2006 | Chen | 600/503 |
| 2008/0128847 A1 * | 6/2008 | Woo | 257/440 |

OTHER PUBLICATIONS

PCT International Search Report and Written Opinion, PCT Application No. PCT/US2005/037043, Feb. 20, 2006, 11 pages.

* cited by examiner

MOTION CANCELLATION OF OPTICAL INPUT SIGNALS FOR PHYSIOLOGICAL PULSE MEASUREMENT

BACKGROUND OF THE INVENTION FIELD OF THE INVENTION

The present invention relates generally to the field of signal processing. More specifically, the present invention is related to pulse rate monitors capable of providing accurate measurement and display of a user's pulse rate during times of physical exercise or other activity.

BACKGROUND OF THE RELATED ART

The accurate measurement of an active person's pulse rate at the wrist is complicated due to the artifacts produced by body motion such as when the person is running or otherwise engaging in physical activity or exercise. Therefore, pulse rate monitors presently in the market utilize chest bands that are worn close to the heart to minimize the effect of motion produced by exercise. Artifacts produced by body motion are detected by pulse rate sensors as "noise" that masks the heart rate pulse signal being measured. In order to mitigate the effects of these artifacts, it is necessary to filter out and cancel as much of the noise signal occurring in the pulse rate frequency band as possible while retaining the desired pulse signal.

Signals of interest are generated by transmitting a light source in the near infrared region into the tissue and measuring the returned signal intensity. Typically two or four light emitting diodes (LEDs) are employed with varying intensity to establish the optimum optical window. The return signal strength will be modulated by the capillary blood flow in the tissue and will vary with the physiologic pulse of the subject. This is a well understood and established principal that has been applied to pulse monitoring equipment for years. Pulse rate sensing taken at locations other than close to the heart, has not been successful because of the relatively low signal strength and relatively high "noise" content. The low signal strength can be attributed to a number of factors including variations in skin and hair density, variations in vascularization, and optical alignment. Further, the received signal includes several components which can be generally classified as "noise" when attempting to sense pulse rate. These high "noise" levels are in addition to classical noise sources present within almost all electrical systems and primarily include inherent optical noise sources, interfering light sources, and motion artifact.

To illustrate, FIG. 1A depicts a signal of interest. FIG. 1B depicts noise caused by motion artifact, interfering lights sources, random noise and the like. FIG. 1C illustrates how the signal of interest is masked by noise due to low signal strength, as an example.

While conventional signal processing techniques may be able to reduce "out of band" noise; that is, noise not found within the frequency of interest, they are challenged to address noise that mimics the signal of interest and that is non-random, the most common of which is motion.

Various pulse rate detection systems are known in the art. U.S. Pat. No. 4,338,950 to Barlow, Jr. et al. discloses an instrument comprised of wrist-mounted unit, which contains a piezoelectric transducer for detecting pulse rate and an accelerometer for detecting body motion during physical activity. The instrument further includes a processor for subtracting the body movement component from the signal, thus yielding the true heart beat signal.

U.S. Pat. No. 5,431,170 to Mathews discloses a device which may be worn on the wrist or hand during physical activity. The device contains a light sensor to measure pulse and light sensor or accelerometer for measuring movement. Mathews discloses that a noise cancellation circuit takes the values from these sensors to give a true pulse signal that is free of pedometry vibration or noise.

U.S. Pat. No. 5,807,267 to Bryars et al. discloses an apparatus which can be combined in a single unit with a wrist watch to display the user's heart pulse rate during physical exercise. A primary piezo sensor detects the heart rate pulse of a user and a background piezo sensor detects the noise from local body motion. Signals from this background sensor are digitally subtracted from the primary pulse sensor thus allegedly reducing the effects of random body noise.

U.S. Pat. No. 6,099,478 to Aoshima et al. disclosse a pulse wave detecting means comprising an LED, photo transistor, or piezoelectric microphone. Body motion detecting means detect body motion using an acceleration sensor. Aoshima et al. disclose that pulse wave extracting means subtract the output of the two sensors to give an accurate pulse rate. Assignee related U.S. Pat. No. 5,776,070 provides similar disclosures.

U.S. Pat. No. 6,129,676 to Odagiri et al. discloses a pulse rate monitor that can be assembled into a wrist watchband and used during activities, such as running. The wrist watchband contains an acceleration sensor to detect action noise and a piezoelectric microphone to detect pulse. When constant motion such as running is detected, the action noise spectrum is subtracted from the pulse wave spectrum, which is depicted in FIGS. 6A-C. Running speed and distance may also be obtained. U.S. Pat. Nos. 5,697,374 and 6,023,662 provide similar disclosures.

U.S. Pat. No. 6,361,501 B1 to Amano et al. discloses a pulse wave diagnosing device formed of device main body having a wristwatch structure, and pulse wave detection sensor unit. A body motion component remover subtracts corrected body motion data from corrected pulse wave data. Body motion waves are detected by an acceleration sensor. This device may be incorporated into a pedometer.

U.S. Patent Appln. Publn. 2005/0116820 A1 to Goldreich discloses a wrist mounted device that detects pulse rates. The vibration sensor is a piezo ceramic sensor that measures movement of the wrist and may include an accelerometer. A physiologic sensor detects the blood pressure pulse rate, and may be fiber optic. Ambient sensors may also be present.

Whatever the precise merits, features, and advantages of the above cited references, none of them achieves or fulfills the purposes of the present invention. For these reasons it would be desirable to provide an improved device and method for accurately measuring pulse rate during physical exercise and other activities.

SUMMARY OF THE INVENTION

It is therefore an object of the present invention to provide a device and method for accurately monitoring and detecting pulse rate.

More particularly, it is an object of the present invention to provide a solution to that allows for adequate removal of inherent optical noise sources, interfering ambient light sources and motion artifact in optical signals especially under intense physical activity.

It is yet another object of the present invention to provide a pulse rate monitor that can distinguish between noise artifact and an individual's true pulse from a signal representing a composite of pulse and noise artifact as illustrated in FIG. 1C.

These and other objects are accomplished in accordance with the present invention, a system and method for measuring a user's pulse rate during physical exercise or activity, that includes a pulse rate sensor having one or more emitters capable of transmitting a light source into body tissue, a photo detector for receiving reflected light from the body tissue and producing a photo detector output signal indicative of the reflected light; an accelerometer for measuring regular motion of the individual and producing an accelerometer output signal indicative of the regular motion; a contact type motion sensor for measuring erratic motion of the individual and producing a piezo sensor output signal indicative of the erratic motion; and a microprocessor for receiving the photo detector output signal, the accelerometer output signal, and the contact type motion sensor output signal, and determining the pulse rate of the individual, where the pulse rate is determined by conditioning the photo detector output signal and removing portions of the conditioned photo detector output caused by regular motion and erratic motion of the individual.

DESCRIPTION OF THE PREFERRED EMBODIMENTS

Figure 1A:
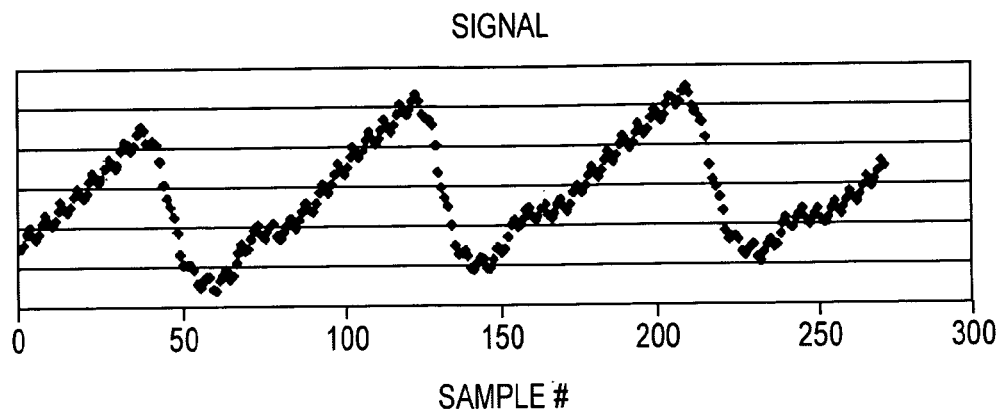
FIG. 1A illustrates a desired optical signal to be measured.
Figure 1B:
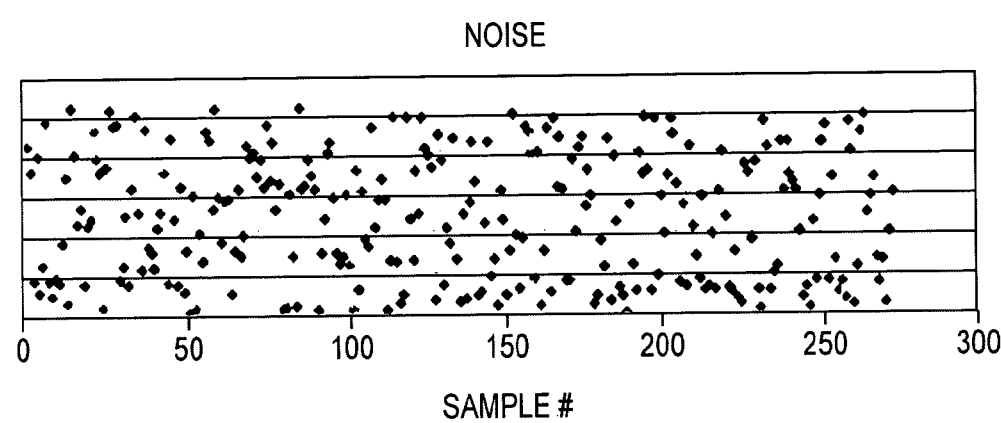
FIG. 1B illustrate noise typically caused by motion.
Figure 1C:
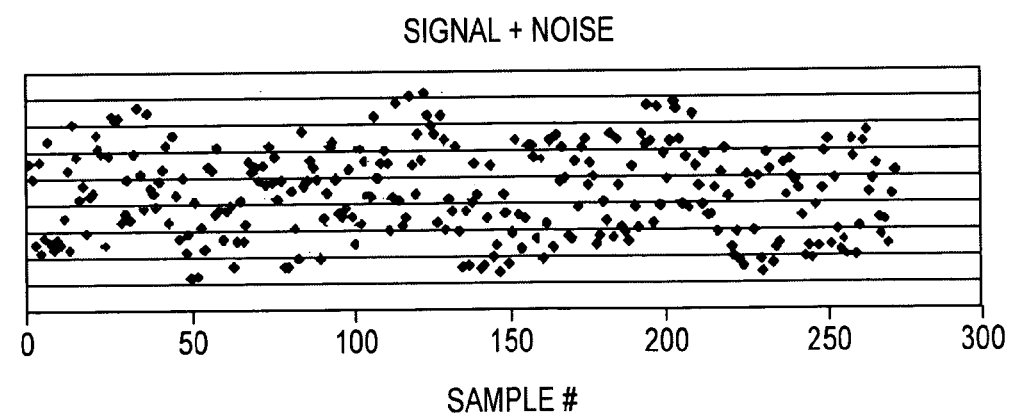
FIG. 1C illustrates the combined optical signal and noise.

While this invention is illustrated and described in a preferred embodiment, the device may be produced in many different configurations, forms and materials. There is depicted in the drawings, and will hereinafter be described in detail, a preferred embodiment of the invention, with the understanding that the present disclosure is to be considered as an exemplification of the principles of the invention and the associated functional specifications for its construction and is not intended to limit the invention to the embodiment illustrated. Those skilled in the art will envision many other possible variations within the scope of the present invention.

Figure 2A:
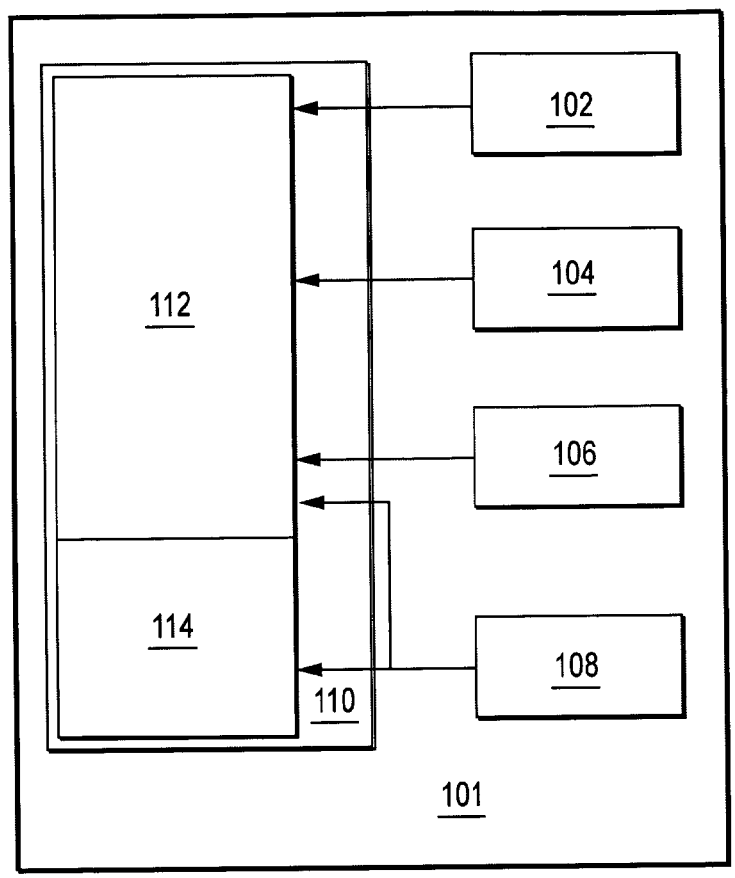
FIG. 2A diagrammatically illustrates a pulse rate sensor in accordance with the present invention.

FIG. 2A illustrates a pulse rate sensor 101 in accordance with the present invention. Emitters 102 (e.g. LED, light emitting diodes) transmit a light source in the near infrared (IR) region into body tissue and a photo detector such as a reflective infra-red sensor 104 that receives the reflected light from the tissue. Pulse rate sensor 101 uses the infrared optical processes from which body volume displacement is analyzed to detect and store pulse rate data, which is indicative of heart rate. Pulse rate sensor 101 also comprises an accelerometer 108, preferably a two-dimensional accelerometer and optionally a three-dimensional accelerometer, that detects periodic or constant motion of the user, and a contact type motion sensor 106 that measures inconsistent or erratic motion of the user, and other movement related sources that effect the optical pulse. The contact type motion sensor can be a piezo sensor or other types of sensors capable of measuring erratic motion such as vibration. The accelerometer or optical sensor output may also be used as input for step counter or pedometer 114. Microprocessor 110 performs signal conditioning functions on the pulse signals received from the photo detector 104, and also samples and filters signals from accelerometer 108 and piezo sensor 106. Pulse rate detector 112 calculates the pulse rate of a user by using conditioned optical pulse signals received by microprocessor 110, filtered signals from accelerometer 108, and piezo sensor 106. While pulse rate detector 112 is shown as being part of microprocessor 110, it is understood that these could also be separate components.

Figure 2B:
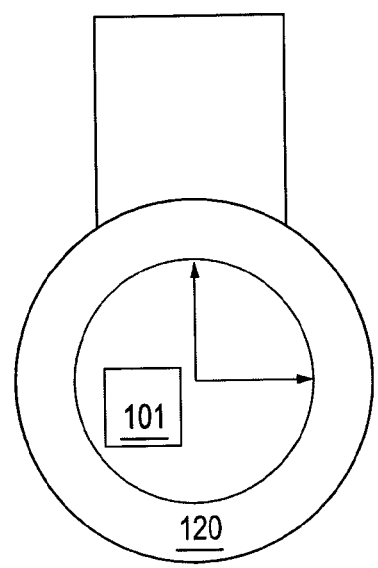
FIG. 2B illustrates a pulse rate sensor encapsulated in a watch module in accordance with the present invention.

Pulse rate sensor 101 may be encapsulated in a watch module 120 as shown in FIG. 2B with an optional rechargeable battery in one embodiment of the present invention. However, other carriers/modules are envisioned as usable with the present invention such as pendants, jewelry, bracelets, patches, music players, etc. which may also contain standard watch functions to include time/date and a stopwatch/timer. These other carriers may be positioned anywhere on the arm of an individual or in the case of a pendants around the neck of an individual. The pulse rate sensor in accordance with the present invention may also include capabilities for firmware updates through the implementation of a software boot loader. Other additions may include a communication module such as universal serial bus (USB) port or an RF receiver/transmitter to automatically upload data to a web portal. Additionally, the pulse rate sensor may include radio frequency identification (RFID) to uniquely identify each watch sold to the web portal.

The pulse rate sensor in accordance with the preferred embodiment of the present invention consists of an optical emitter including of one or more light emitting diodes, an optical receiver, active signal conditioning, an accelerometer and a piezo sensor, and a microprocessor. The microprocessor controls the active signal conditioning applied to the optical sensor by automatically adjusting the light emitting diode output to maintain the optimal signal strength, controlling the amplification of the received signal, and automatically removing the direct current bias of the received signal. The conditioned optical sensor output and the accelerometer and piezo sensor outputs are sampled as input to two different pulse rate calculators, one used when there is no motion present and the other used when there is motion present. The piezo sensor is used to detect erratic motion while the accelerometer is used to detect periodic motion.

As further described below, pulse rate signal degradation due to arm motion and skin vibrations is diminished through a combination of algorithms that control signal boosting, waveform refinement and signal noise suppression.

Figure 3:
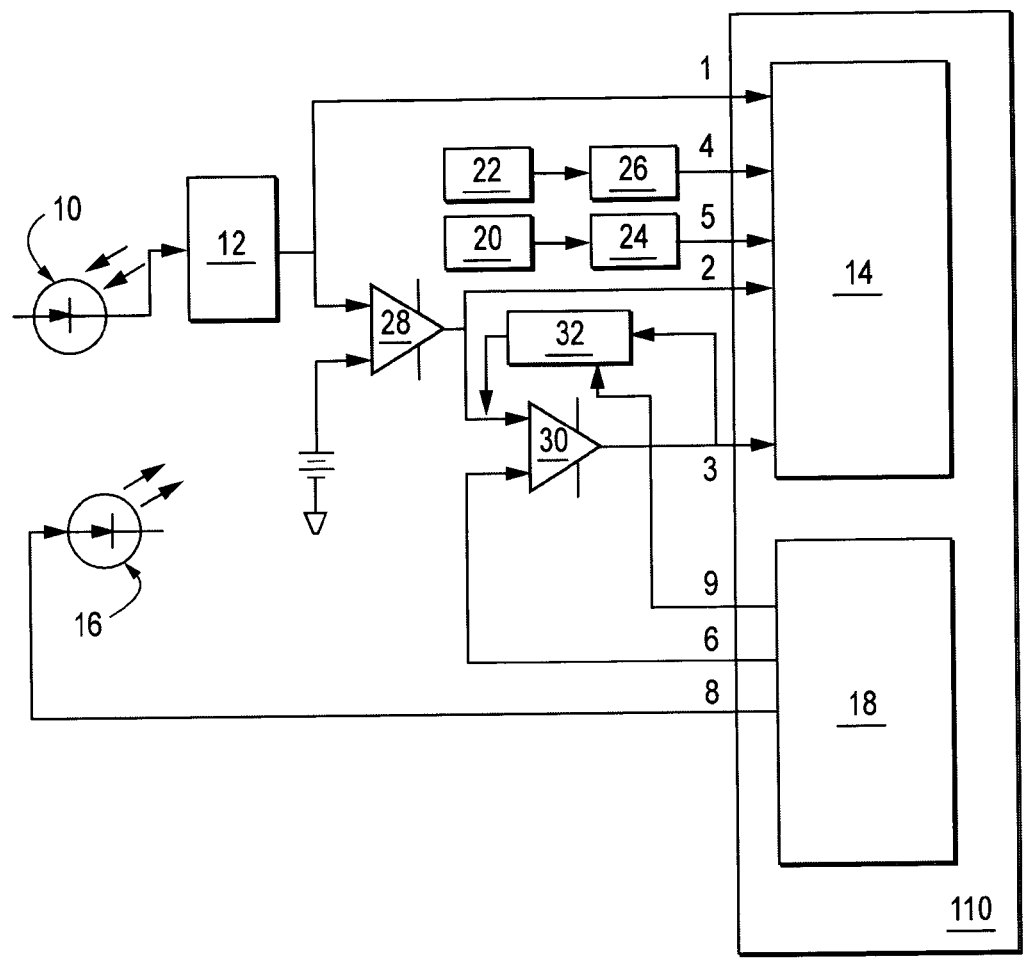
FIG. 3 illustrates the signal conditioning process for an optical signal in accordance with the present invention.

Referring to FIG. 3, the process to achieve signal conditioning of the pulse signal output from photo detector 10 in accordance with the present invention is illustrated. A pulse signal output from photo detector 10, which may be a reflective infrared sensor, is filtered through low pass filter 12 and is provided to input 1 of the microprocessor 110, which includes an internal analog to digital convertor.14. Naturally, analog to digital converter 14 could also be a component separate from microprocessor 110. Through this connection, microprocessor 110 is able to monitor the output from photo detector 10 and to determine the appropriate intensity for an infrared light emitting diode 16, which transmits optical signals into body tissue. The intensity of infrared light emitting diode 16 is programmable using an output 8 from a digital to analog converter 18 within microprocessor 110 (again, digital to analog converter 18 could also be a component separate from microprocessor 110). As further discussed below, an internal closed loop control function within the microprocessor 110 maintains the proper intensity of the infrared light emitting diode 16 using the feedback from the photodector 10 at input 1 to control output 8. Using this control function, the output signal from photodetector 10 is in an appropriate range for direct current compensation and other related functions. Further, this intensity control allows the microprocessor 110 to periodically adjust the system to account for different environmental and physiological conditions, including varying ambient light levels, long term blood flow changes and varying responses from user to user. The pulse signal transmitted from photodetector 10 is filtered through a lowpass filter 12 of approximately 10 Hz to reduce inherent noise.

The pulse signal from photodetector 10 generally includes a large direct current component that represents gross blood flow, and a small alternating current component that represents true pulse. Because it is desirable to accurately measure true pulse, active signal conditioning including additional amplification of the alternating current component and compensation of the direct current component is necessary. Compensation of the direct current component occurs in two stages. The first stage is accomplished using an amplifier 28 to achieve a fixed signal gain. The output from this first stage is provided to microprocessor 110 at input 2. The second stage is the programmable gain stage utilizing a second amplifier 30 with output to microprocessor 110 shown at 3. A fixed direct current compensation voltage, shown at output 7, is subtracted from the filtered pulse signal provided from filter 12. Amplifier 28 has a fixed gain and is output to the microprocesser 110 at 2. The amplification and DC adjustment provided by amplifier 28 moves the signal level of its output to the midrange of second operational amplifier 30 and allows for a second stage of amplification. The amplification gain 32 associated with second amplifier 30 is programmable to allow for adjust necessary to deal with varying pulse strengths. The gain 32 is periodically adjusted by the microprocessor 110 to maintain signal integrity. A programmable direct current compensation signal from output 6 is also applied to second amplifier 30 by microprocessor 110. It is during this second stage that the sensor signal is significantly amplified. The programmable direct current compensation at output 6 is adjusted with every sample of the first stage gain signal or input 2 of the analog to digital convertor. The microprocessor calculates the direct current value of the optical pulse signal, and applies that value using output 6 as the reference at the input of the amplifier stage 30. This is a fine adjustment and allows for the quick recovery of the pulse signal during and after motion. As significant amplification is applied to the input signal at second amplifier 32, the programmable direct current compensation further helps to center the signal at the amplifier input, and prevents second amplifier 32 from saturating during periods of motion by the user. Thus, the pulse can be more accurately tracked during periods of motion.

Referring again to FIG. 4, the steps used to control the direct current compensation signal 6 and the optical emitter supply signal 8 are described below.

1) The optical sensor output signal, first amplifer output signal, and second amplifer output signal are all oversampled at inputs 1, 2, and 3 as shown in FIG. 2 to generate samples x1($i$), x2($i$), x3($i$) where i represents the $i^{th}$ sample.

2) The signals are all filtered to produce a smoother signal at a lower sample rate. More specifically, the oversampled signals are processed as follows:

$$\text{Smoothx1}(j) = (1/X) * \Sigma_{j=i}^{x} x1(i); X = \text{number of points}$$

$$\text{smoothx2}(j) = (1/X) * \Sigma_{j=i}^{x} x2(i); X = \text{number of points}$$

$$\text{smoothx3}(j) = (1/X) * \Sigma_{j=i}^{x} x3(i); X = \text{number of points}$$

The filtered sample signal (smoothx1($j$)) is used for the automatic optical emitter control at signal 8. The filtered first amplifier output signal (smoothx2($j$)) and the filtered second amplifier output signal (smoothx3($j$)) are used for automatic direct current compensation at signal 6 and for pulse detection, respectively.

3) Automatic control of optical emitter 16 is based on the filtered second amplifier output signal at input 1, and is applied as follows on a periodic basis.
 a) If smooth1($j$)>expected range, then decrease output at signal 8.
 b) If smooth1($j$)<expected range, then increase output at signal 8.

4) Direct current compensation is applied at output 6 as follows at the update rate of the smoothing filters as follows.
 a) If smooth3($j$)>(max value of smooth3($j$)–threshold), then Direct current compensation(j)=smooth2($j$)
 b) Else if smooth3($j$)<(min value of smooth3($j$)+threshold), then Direct current compensation(j)=smooth2($j$)
 c) Else direct current compensation(j)=direct current compensation(j–1).

Figure 5:
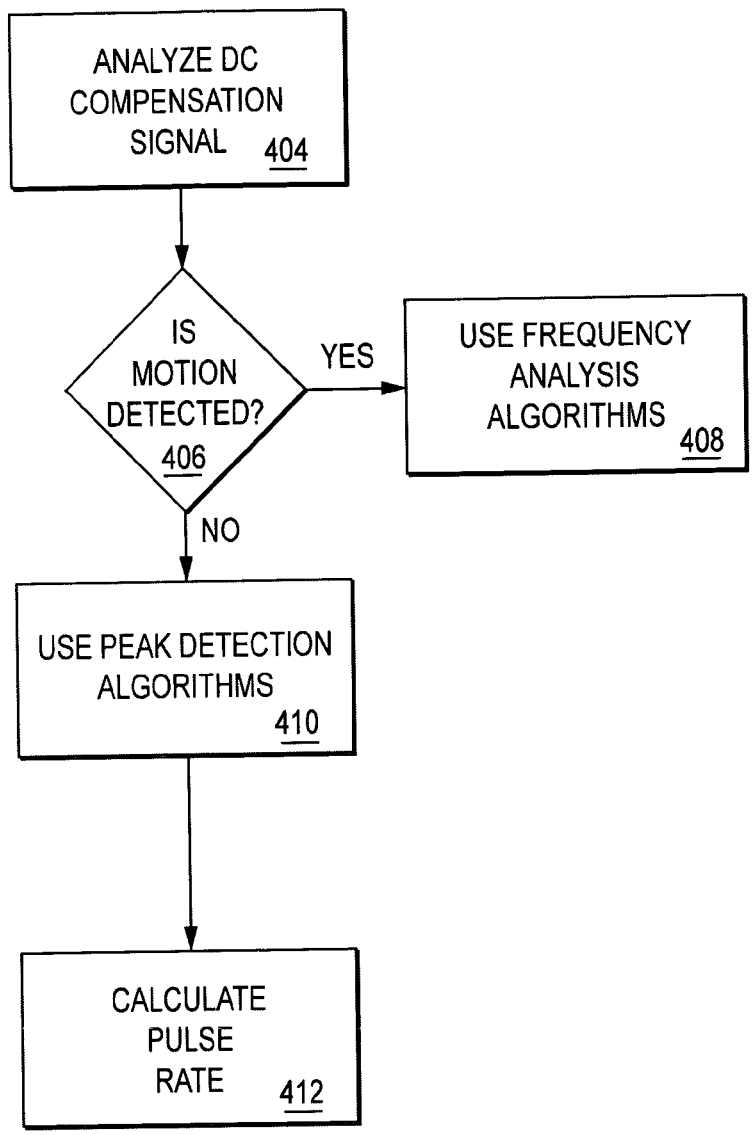
FIG. 5 illustrates a flowchart depicting steps followed to calculate pulse rate in accordance with the present invention.

During periods of motion, the signal applied for direct current compensation at output 6 by the microprocessor is correlated to the motion of the user. As result, the direct current compensation can also be used as an indicator of motion as shown in FIG. 5. The direct current compensation signal is first analyzed in step 404, and this analysis is used to detect motion in step 406. If the direct current compensation is stable or lacks change this indicates a lack of motion and then the peak detection algorithm 410 described below is used to calculate the pulse rate 412. This allows for a fast recovery of the pulse rate after periods of motion. If the direct current compensation is correcting the signal, this indicates that motion is present and the frequency based algorithm 408 described below is used to calculate the pulse rate 412.

The direct current compensation(j) signal is used for motion discrimination in block 406 and determines whether peak detection algorithms can be used, for example during periods of no motion, or if frequency analysis is necessary for example during periods of motion. Stated alternatively, the direct current compensation(j) signal is used to determine whether to apply peak detection algorithms in block 408 or frequency analysis in block 410 to determine the pulse rate. More specifically, if direct current compensation(j) has not changed for the past 3×(1/pulse rate) seconds during which pulse rate is being measured, then the peak detection algorithm described below is used.

If direct current compensation(j) has changed during the past 3×(1/pulse rate) seconds during which pulse rate is being measured the frequency analysis algorithm described below is used.

Peak detection is calculated as follows:
1) A first derivative calculated as diff1($i$)=smoothx2($i$)–smoothx2($i$–1) is taken over the filtered signal.
2) A second derivative, diff2($i$)=diff1($i$)–diff1($i$–1), is calculated or computed from the first derivative.
3) Peak detection is analyzed using the first and second derivatives to find the peaks within the filtered signal.

If diff1($i$)=0 and diff2($i$)<0 then peak($i$)=$i$

If diff1($i$) does not=0 and diff2($i$)>0 then peak($i$)=0 where a non-zero value indicates a peak in the filtered signal and a zero indicates no peak.

4) The instantaneous pulse rate is calculated in block 412 as the difference between peaks in the filtered signal.

Instantaneous pulse rate(i)=sample rate (in hz)/Period (peak(i)–previous non-zero(peak(i)))*60 sec/minute.

Figure 4:
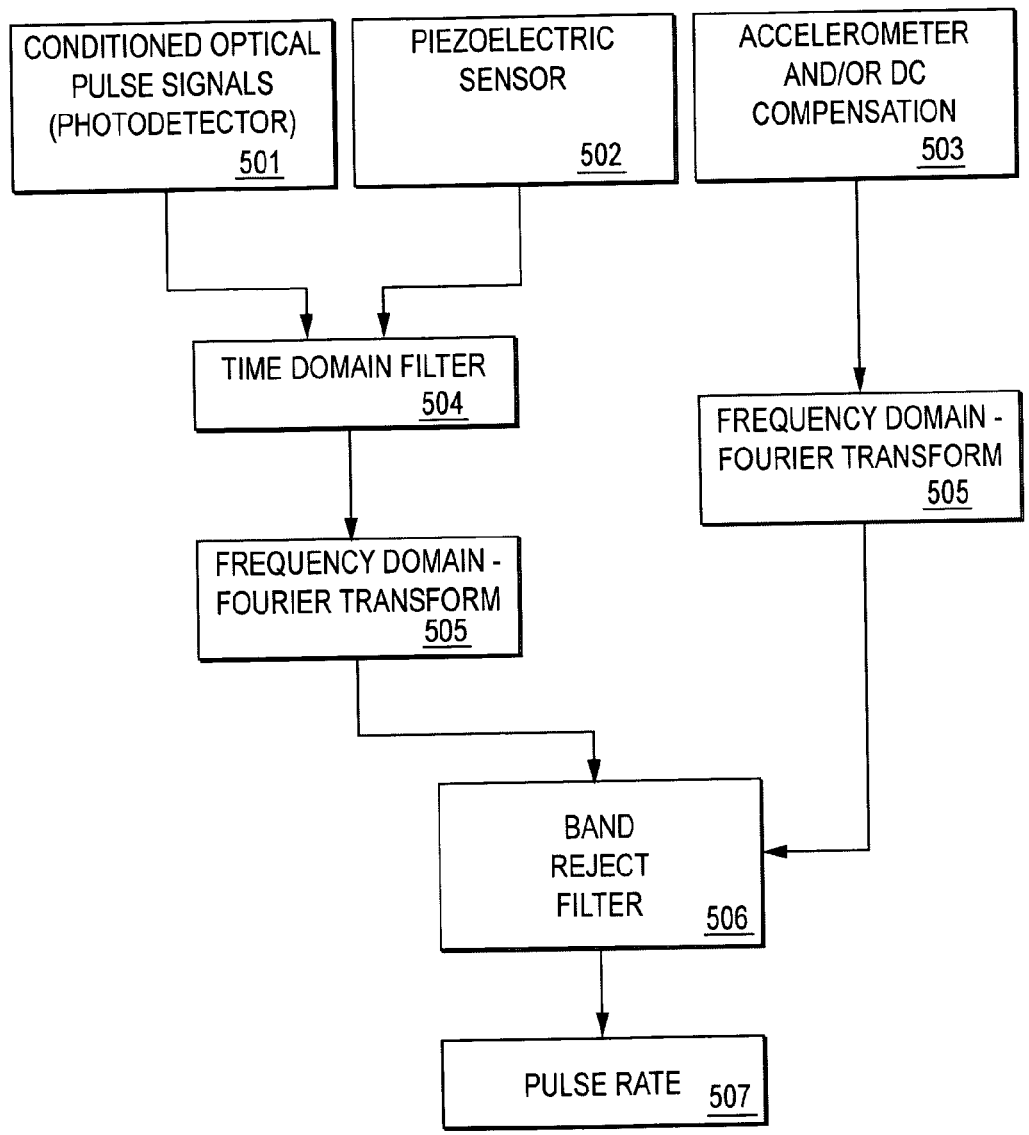
FIG. 4 illustrates a flowchart depicting the motion discrimination process in accordance with the present invention.

Referring back to FIG. 3, the pulse detection system also includes an accelerometer 20 and piezo sensor 22. Signals from accelerometer 20 and piezo sensor 22 are filtered through lowpass filters 24, 26 at analog to digital inputs 5 and 4, respectively before being sampled. The accelerometer 20 is used in the motion mitigation fast fourier transform (FFT) algorithms and the piezo sensor is an indicator of erratic motion as shown in FIG. 4. Generally speaking, the accelerometer 20 and piezo sensor 22 are used to remove the motion artifacts from the optical sensor output present during motion of the user. When substantial erratic or momentary motion is detected using the piezo sensor 22, the information is used to filter the optical sensor output in the time domain so that the signal is not used for pulse rate calculations during the erratic motion 504. Additional filtering may also be applied to the instantaneous pulse rate to provide a more stable pulse rate output. Periodic motion is detected by analyzing the accelerometer output signal in the frequency domain 505 and this information is used to generate a band reject filter which is applied to the optical sensor output in the frequency domain 506.

If it is determined that motion is present, a frequency algorithm as shown in FIG. 4 is used. The signals that undergo frequency analysis are the smoothed first amplifier output signal (smoothx2) and the smoothed second amplifier output signal (smoothx3) in step 501. Signals from the accelerometer 20 and direct current compensation are also provided in step 503 so that further frequency analysis can be done. Frequency analysis may include all or a subset of the foregoing signals. The frequency bins will be analyzed to determine whether motion frequencies are present. Again, motion frequencies are determined by the accelerometer output or the direct current compensation signal. The motion frequencies are then removed from the sensor signals, smoothx2 and smoothx3 to allow for discrimination of the pulse rate as follows:

a) Apply a ten second window filter to smoothx2, smoothx3, accelerometer, and direct current compensation b) Remove data as necessary if erratic motion is detected in the time domain at step 504 c) Apply frequency translation to all or a subset of windowed smoothx2, smoothx3, accelerometer, and direct current compensation in step 505;

d) Band pass filter all signals in the range of 0.5 Hz to 4 Hz at step 506;

e) Identify frequency peaks in smoothx2, smoothx3, accelerometer, and DC compensation;

f) Using the frequency peaks from the accelerometer of direct current compensation to determine the frequencies to reject, using band reject filter, from smoothx2 and smoothx3 at step 506;

g) Remove peaks from smoothx3 that are not common with those in smoothx2; and h) Pulse rate equals the lowest frequency peak in smoothx3 (block 507)

If no peaks are remaining, the pulse rate is not updated.

It is anticipated that the present invention may also be used as a pedometer. To use the pulse rate monitor wrist watch as a pedometer, the data from the two-axis accelerometer is filtered. If the motion detected is a "step," i.e. foot motion, the filter applied to the Y-axis accelerometer data should be one-half that applied to the X-axis accelerometer data. Peak detection, i.e. detecting the intervals between the peaks of the signals from the X and Y accelerometers, is used to determine the fundamental frequencies of motion. Peaks are detected using the first and second derivative methods described above.

The pulse rate is output using a digital signal which transitions at the rate of the pulse rate. The pedometer is output using a digital signal which transitions once for each step detected.

A system and method for the effective implementation of motion cancellation of optical input signals for physiological pulse measurement in accordance with the present invention has been disclosed herein. While various preferred embodiments have been shown and described, it will be understood that there is no intent to limit the invention by such disclosure, but rather, it is intended to cover all modifications and alternate constructions falling within the spirit and scope of the invention, as defined in the appended claims.

We claim:

1. A pulse rate sensor for measuring a physiological parameter of an individual comprising:
   an optical emitter for transmitting light from a light source into body tissue;
   a photo detector for receiving reflected light from said body tissue and producing a pulse signal indicative of reflected light;
   an accelerometer for measuring regular motion of the individual and producing an accelerometer output signal indicative of the regular motion;
   a piezo sensor for measuring erratic motion of the user and producing a contact type motion sensor output signal indicative of the erratic motion; and
   a microprocessor for receiving the pulse signal, the accelerometer output signal, and the piezo sensor output signal, and determining the pulse rate of the individual, wherein the pulse rate is determined by:
     conditioning the pulse signal wherein conditioning comprises:
       sampling and filtering said pulse signals with a non-adaptive low-pass filter to produce filtered signals;
       applying direct current compensation to said filtered signals;
       discriminating motion based on said direct current compensation signal; and
       if no motion is detected, applying peak detection algorithms to calculate said pulse rate, else applying frequency analysis algorithms to calculate said pulse rate wherein said peak detection algorithms comprise:
         taking a first derivative over said filtered signal;
         computing a second derivative from said first derivative; finding peaks within said filtered signal using said first and second derivatives; and
         calculating instantaneous pulse rate as the difference between peaks in said filtered signal;
     and removing portions of the conditioned pulse signal caused by regular motion and erratic motion of the individual.

2. The pulse rate sensor of claim 1 wherein said transmitted light source lies in the near infrared region, the emitter comprises a plurality of light emitting diodes, the photo detector is a reflective infrared sensor and the accelerometer is a two-dimensional accelerometer.

3. The pulse rate sensor of claim 1 wherein said sensor is encapsulated in a watch module for wrist-based sensing.

4. The pulse rate sensor of claim 3 wherein said watch module includes a universal serial bus port to automatically upload data, a radio frequency identification tag to uniquely identify said watch module, wherein said watch module is further capable of receiving firmware updates.

5. The pulse rate sensor of claim 1 wherein said contact type motion sensor comprises a piezo sensor and said contact type motion sensor output signal comprises a piezo sensor output signal.

6. The pulse rate sensor of claim 1 wherein the microprocessor removes portions of the conditioned photo detector output caused by regular motion and erratic motion of the individual by transforming the photo detector output signal, the accelerometer output signal, and the piezo sensor output signal to the frequency domain and removing unwanted frequency components.

7. The pulse rate sensor of claim 1 wherein the conditioning step for determining pulse rate further comprises:
   automatically adjusting output of the light source to maintain optimal signal strength of the pulse signal.

8. The pulse rate sensor of claim 1 wherein the step of applying direct compensation to said filtered signals signal comprises:
   subtracting a fixed direct current compensation from the photo detector output signal to produce a DC adjusted photo detector output signal and amplifying the DC adjusted photo detector output signal to produce an output (2); and
   applying a programmable direct current compensation to the output (2) to produce a DC adjusted output (3) and amplifying the DC adjusted output (3) to produce an output (4).

\* \* \* \* \*